(12) United States Patent
Chia (10) Patent No.: US 7,579,144 B2
(45) Date of Patent: Aug. 25, 2009

(54) METHODS FOR DIAGNOSING CHRONIC FATIGUE SYNDROME

(75) Inventor: John K. S. Chia, Lomita, CA (US)

(73) Assignee: EV Med Research, Lomita, CA (US)

( * ) Notice: Subject to any disclaimer, the term of this patent is extended or adjusted under 35 U.S.C. 154(b) by 0 days.

(21) Appl. No.: 11/929,775

(22) Filed: Oct. 30, 2007

(65) Prior Publication Data

US 2008/0102447 A1 May 1, 2008

Related U.S. Application Data

(60) Provisional application No. 60/863,437, filed on Oct. 30, 2006.

(51) Int. Cl.
*C12Q 1/68* (2006.01)
*A61K 39/00* (2006.01)
(52) U.S. Cl. .................. 435/5; 424/204.1; 424/217.1
(58) Field of Classification Search ............ 435/6, 435/7.1
See application file for complete search history.

(56) References Cited

U.S. PATENT DOCUMENTS

2007/0160999 A1* 7/2007 Calabrese ................ 435/6

OTHER PUBLICATIONS

Galbraith et al. J. Gene. Virol. 1995, vol. 76, pp. 1701-1707.*
Cinti et al. Inter. J. Obesity 2000, vol. 24, pp. 789-793.*
Romero J. Arch Patho. Lab. Meth. 1999, vol. 123 pp. 1691-1169.*
Fukuda K, Straus SE, Hickie I, et al and the International Chronic Fatigue Syndrome Study Group. The chronic fatigue syndrome: a comprehensive approach to its definition and study. Ann Intern Med. 1994;121:953-59.
Reeves WC et al. Identification of ambiguities in the 1994 chronic fatigue syndrome research case definition and recommendations for resolution. BMC Health Serv Res. 2003;3:25-9.
Levy JA. Viral studies of chronic fatigue syndrome: Introduction. Clin Infect Dis. 1994;18(suppl 1):S117-2.
Chia JKS, Chia LY. Chronic *Chlamydia pneumoniae* infection, a treatable cause of chronic fatigue syndrome. Clin Infect Dis. 1999;29:452-3.
Lerner MA, Zervos M, Dworkin HJ, Chang CH, Fitzgerald JT, Goldstein J, Lawrie-Hoppen C. et al. New cardiomyopathy: pilot study of intravenous ganciclovir in a subset of chronic fatigue syndrome. Infect Dis. Clin Prac. 1997;6:110-117.
Kerr JR, Cunniffe VS, Kelleher P, Berstein RM, Bruce IN. Successful intravenous immunoglobulin therapy in 3 cases of Parvovirus B19-associated chronic fatigue syndrome. Clin Infect Dis. 2003;36:e100-6.
Chia JKS, Jackson B. Myocarditis due to parvovirus B19 in an adult patient. Clin Infect Dis. 1996;23:200-1.
Chia JK, Chia A. Diverse etiologies for the chronic fatigue syndrome. Clin Infect Dis. 2003;36:671-2.
Yousef GE, Mann GF, Smith DF, Bell EJ, McCartney RA. Chronic enterovirus infection in patients with postviral fatigue syndrome. Lancet 1988;1:146-7.
Landay AL, Jessop C, Lennette ET, Levy JA. Chronic fatigue syndrome: clinical condition associated with immune activation. Lancet 1991;338:707-12.
Miller NA, Carmichael HA, Calder BD, et al. Antibody to Coxsackie B virus in diagnosing post-viral fatigue syndrome. BMJJ;302:140-3.
Halpin D, Wessely S. VP1 antigen in chronic postviral fatigue syndrome (letter). Lancet 1989; 1:1028-1029.
Manian FA. Simultaneous measurement of antibodies to Epstein-Barr virus, human herpesvirus 6, herpex simplex virus type 1 and 2, and 14 enteroviruses in chronic fatigue syndrome: is there evidence of activation of a nonspecific polyclonal immune response. Clin Infect Dis. 1994:19:448-53.
Swanink CM, Melchers WJ, van der Meer JW, Vercoulen JH, Bleijenberg G, Fennis JF, Galama JM. Enterovirus and the chronic fatigue syndrome. Clin Infect Dis 1994;19:860-4.
Minor PD, Bell EJ(1990): Picornaviridae. In :Principle of bacteriology, virology and immunology, 8th edition. Collier LH, Timbury MC (eds). London: Arnold Publisher, pp. 323-356.
Nairn C, Galbraith DN, Clements GB. Comparison of Coxsackie B neutralization and enteroviral PCR in chronic fatigue patients. J Med Virol. 1995 46:310-313.
Behan PO, Behan WMH, Bell Ej. The post-viral fatigue syndrome-an analysis of the findings in 50 cases. J Infect. 1985;10:211-222.
Gow JW, Behan WMH, Clements GB, Woodall C, Riding M, Behan PO. Enteroviral RNA sequences detected by polymerase chain reaction in muscle of patients with post-viral fatigue syndrome. BMJ 1991;302:692-6.
Gow JW, Behan WMH, Simpson K, McGarry F, Keir S, and Behan PO. Studies on enterovirus in patients with chronic fatigue syndrome. Clin Infect Dis 1994;18 (Suppl):S126-129.
Yousef GE, Isenberg DA, Mowbray JF. Detection of enteroviral-specific RNA sequence in muscle biopsy specimens from patients with adult-onset myositis. Ann Rheum Dis 1990;49:310-5.
Cunningham L, Bowles NE, Lane RJM, Dubowitz V, Achard LC. Persistence of enteroviral RNA in chronic fatigue syndrome is associated with abnormal production of equal amounts of positive and negative strands of enteroviral RNA. J Gen Virol. 1990;71, 1399-1402.
McArdle A, McArdle F, Jackson MJ, Page SF, Fahal I, Edwards RH. Investigation by polymerase chain reaction of enteroviral infection in patients with chronic fatigue syndrome. Clin Sci. 1996;90:295-300.
Lindh G, Samuelson A, Hedlund KO, Evengard B, Lindquist L, Ehrnst A. No. finding of enteroviruses in Swedish patients with chronic fatigue syndrome. Scan J Infect Dis 1996;28:305-7.
Lane RJ, Soteriou BA, Zhang H, Archard LC. Enterovirus related metabolic myopathy: a postviral fatigue syndrome. J Neurol Neurosurg Psychiatry 2003;74:1382-6.
Douche-Aourik F. et al. Detection of enterovirus to human skeletal muscle from patients with chronic inflammatory muscle disease or fibromyalgia and healthy subjects. J Med Virol. 2003;71:540-7.

(Continued)

*Primary Examiner*—Gary B. Nickol
*Assistant Examiner*—Bao Qun Li
(74) *Attorney, Agent, or Firm*—K&L Gates LLP; Louis C. Cullman; Michelle S. Glasky (57) ABSTRACT

Methods are provided for detecting enteroviral antigens in the stomach of patients having symptoms consistent with chronic fatigue syndrome (CFS). The presence of enteroviral viral antigens in the stomach of these patients is then correlated with the patients' symptoms to establish a diagnosis of CFS.

6 Claims, 3 Drawing Sheets

OTHER PUBLICATIONS

Chia JK, Jou NS, Majera L, et al. The presence of enteroviral RNA (EV RNA) in peripheral blood mononuclear cells (PBMC) of patients with the chronic fatigue syndrome (CFS) associated with high levels of neutralizing antibodies to enteroviruses. Abstract 405, Clin Infect Dis. 2001;33:1157.

Chia J, Chia A. Detection of enteroviral RNA in the peripheral blood leukocytes of patients with the chronic fatigue syndrome. Abstract 763. In: Program and abstracts of the 40th annual meeting of the Infectious Diseases Society of America. Chicago, Illinois. IDSA 2002:178.

Chia J, Chia A. Detection of double-stranded RNA in the peripheral blood leukocytes of patients with the chronic fatigue syndrome. Abstract T-101. In Program of the 104th General Meeting for the American Society of Microbiology. New Orleans, Louisiana, 2004.

Chia J, Chia A. Ribavirin and Interferon α for the treatment of patients with chronic fatigue syndrome associated with chronic Coxsackievirus B infection: a preliminary observation. J. Appl. Research. 2004;4:286-292.

Chia, JK. The role of enterovirus in chronic fatigue syndrome. J. Clin. Path. 2005;58:1126-1132.

Henningsen P et al. Medically unexplained physical symptoms, anxiety and depression: a meta-analytic review. Psychosomatic Medicine 65:528-33, 2003.

Frissora CL and Koch KL. Symptom overlap and comorbidity of irritable bowel syndrome with other conditions. Current Gastroenterology Reports 7:264-271, 2005.

Carruthers BM et al. Myalgic encephalomyelitis/chronic fatigue syndrome: clinical working case definition, diagnostic and treatment protocols. Journal of Chronic Fatigue Syndrome 11:7-115, 2003.

Chia JKS and Chia AY. Chronic fatigue syndrome is associated with chronic enterovirus infection of the stomach. J. Clin. Pathol. 61:43-8, 2008.

* cited by examiner

SEQUENCE LISTING

<160> NUMBER OF SEQ ID NOS: 3

<210> SEQ ID NO 1
<211> LENGTH: 15
<212> TYPE: PRT
<213> ORGANISM: Enterovirus sp.

<400> SEQUENCE: 1

Pro Ala Leu Thr Ala Val Glu Thr Gly Ala Thr Asn Pro Leu Val

-continued

```
1               5              10             15

<210> SEQ ID NO 2
<211> LENGTH: 21
<212> TYPE: DNA
<213> ORGANISM: Enterovirus sp.

<400> SEQUENCE: 2
cctccggccg aatgcggcta a                                          21

<210> SEQ ID NO 3
<211> LENGTH: 22
<212> TYPE: DNA
<213> ORGANISM: Enterovirus sp.

<400> SEQUENCE: 3
caattgtcac cataagcagc ca                                         22
```

METHODS FOR DIAGNOSING CHRONIC FATIGUE SYNDROME

CROSS REFERENCE TO RELATED APPLICATIONS

The present application claims the benefit under 35 U.S.C. §119(e) of U.S. Provisional Patent Application No. 60/863,437 filed Oct. 30, 2006 which is incorporated by reference herein in its entirety.

FIELD OF THE INVENTION

The present invention relates to methods for diagnosing chronic fatigue syndrome. More specifically the present invention provides methods for detecting enterovirus antigens in stomach tissue and correlating the findings with clinical symptoms to establish a diagnosis of chronic fatigue.

REFERENCES

Through out this specification references will be cited using numbers inserted parenthetically. These reference numbers correspond to the References Cited section immediately preceding the claims. Each reference is herein specifically incorporated by reference for all it teaches related method and materials related to diagnostic virology and chronic fatigue syndrome.

BACKGROUND OF THE INVENTION

Chronic fatigue syndrome (CFS) has been a true challenge for the practicing physicians and scientific researchers. The constellation of symptoms is complex and many patients present differently (1, 2). A severe flu-like illness that occurred in the majority of cases of CFS followed by persistent illness and fatigue suggest an infectious etiology triggering and possibly perpetuating this syndrome. In small subsets of patients, Epstein-Barr virus (EBV), Cytomegalovirus (CMV), Parvovirus B19, *Brucella, Toxoplasma, Coxiella burnetti* and *Chlamydia pneumoniae* have been reported to cause prolonged fatigue, fevers and many other symptoms of CFS (3-9). However, no direct nexus between these etiological agents and CFS has been established.

Some studies demonstrated circulating antigen of enterovirus and elevated antibody titers (10-15) suggesting a role for enteroviruses in CFS. A number of investigators used DNA/RNA hybridization or polymerase chain reaction (PCR) to detect the presence of enteroviral RNA in the blood and muscles of patients with CFS (17-22). Yousef reported Coxsackie Virus B (CVB) RNA persistence in muscle fibers in 6 out 13 (46%) adult patients with dermatomyositis or polymyositis using in situ hybridization (21). The enteroviral RNA was usually, but not always, found in sections with inflammatory cells. Cunningham tested muscle biopsy specimens from CFS patients to demonstrate that the enteroviral RNA found in patient material had a positive:negative strain ratio of 1:1 rather than the 100:1 ratio found in control enteroviral cultures (22). This result suggested a defect in control of enteroviral RNA synthesis in CFS patients that might permit persistence of the defective virus in these patients. Galbraith et al. extend the above finding by performing phylogenetic analysis of the amplified cDNA from the blood of patients; the sequences closed matched to those found in CVB and Echoviruses (23). A number of other studies have failed to demonstrate amplifiable enteroviral RNA in blood or in other tissue (24-25), although two recent papers again demonstrated the presence of enteroviral RNA in muscle biopsies of CFS patients and not in the controls (26, 27).

The present inventor has recently demonstrated the presence of enteroviral RNA in the peripheral blood leukocytes of 35% of the CFS patients, and the persistence of enteroviral RNA correlated with the severity of illness (28-30). Antiviral treatment with interferon and Ribavirin and the combination of α- and γ-interferon resulted in significant improvement of symptoms and suppression of viral RNA in the blood leukocytes (31-32). The relapse of symptoms and reappearance of viral RNA in the peripheral blood leukocytes after drug discontinuation supported the pathogenic role of enterovirus in CFS.

However, there remains a need for sensitive and specific methods for the diagnosis of chronic enterovirus infection in immunocompetent hosts. Enteroviruses cause acute respiratory and gastrointestinal infections, with subsequent dissemination to the central nervous system, heart and muscles. Previous studies looked for viral products in the blood or in the end-organs have yielded conflicting results. Being acid-resistant, swallowed, infected secretions from upper airway, or virus-contaminated water/food may survive in the stomach and cause acute infections of the stomach. Most of the CFS patients complained of upper and lower gastrointestinal symptoms, which are often referred to as irritable bowel syndrome. Stomach tissue is easily accessible by upper gastrointestinal endoscopy (EGD) and biopsy of the antrum is routinely performed to look for *Helicobacter pylori*—an established pathogen of the stomach.

SUMMARY OF THE INVENTION

The present invention provides methods for demonstrating the persistence of enterovirus in the stomach as a diagnostic test for chronic fatigue syndrome. More specifically, the present invention provides a testing procedure to identify enterovirus viral capsid protein (VP1), viral RNA and cultivable virus in a biopsy of stomach tissue. Positive laboratory results are then correlated with recognized clinical symptoms to establish a diagnosis of chronic fatigue syndrome (CFS).

In one embodiment of the present invention, a method for diagnosing CFS in a human patient is provided comprising detecting enteroviruses in the stomach tissue of a patient having symptoms consistent with CFS wherein the symptoms consist of persistent fatigue for at least six months and at least four further symptoms selected from the group consisting of cognitive dysfunction, post-exertional malaise, unrefreshing sleep, joint pain, persistent muscle pain, headaches, tender cervical or axillary lymph nodes and sore throat and correlating the detection of enterovirus with clinical symptoms to establish a diagnosis of CFS in the patient.

In another embodiment of the present invention, the method includes detecting enteroviral capsid protein (VP1) or enteroviral viral RNA in the stomach tissue of the patient and correlating the detection of enterovirus with clinical symptoms to establish a diagnosis of CFS.

In yet another embodiment of the present invention, a non-cytopathic enterovirus is detected in the stomach tissue of the patient and the detection of enterovirus is correlated with clinical symptoms to establish a diagnosis of CFS.

In still another embodiment of the present invention, immunoperoxidase or immunofluorescent staining of stomach tissue is used to detect enteroviral antigens in the patient and the detection of enterovirus is correlated with clinical symptoms to establish a diagnosis of CFS.

Another embodiment of the present invention comprises detecting viral RNA within stomach tissue samples using RT-PCR of the patient and correlating the detection of enterovirus with clinical symptoms to establish a diagnosis of CFS.

Still another method of the present invention comprises detecting enteroviral antigens in the stomach of a CFS patient using viral cultures and correlating the detection of enterovirus with clinical symptoms to establish a diagnosis of CFS.

In one embodiment of the present invention, the correlating step comprising correlating the degree of staining or the viral load with the severity of the symptoms of CFS. In another embodiment, the degree of staining or the viral load is inversely correlated with the ability to work.

Other detection methods known to those skilled in the art of diagnostic virology will be readily apparent to the skilled virologist and are considered within the scope of the present invention when used in conjunction with correlating the detection of enterovirus with clinical symptoms to establish a diagnosis of CFS.

BRIEF DESCRIPTION OF THE FIGURES

FIG. 4A: 2+ staining with 5D8/1 FIG. 4B: same specimen as FIG. 4A demonstrating no staining with anti-cytomegalovirus (CMV) mAb (100× magnification); FIGS. 4C and 4D: 1+ staining with 5D8/1 mAb at 100× (FIG. 4C) and 400× (FIG. 4D) magnification.

FIG. 5A: 0 ng peptide inhibitor or 10 mg bovine serum albumin; FIG. 5B-5D: increasing inhibition of mAb binding in the presence of 1 ng (FIG. 5B), 10 ng (FIG. 5C) and 100 ng (FIG. 5D) of peptide inhibitor. 100× magnification.

FIGS. 6A and 6B: staining of antrum biopsy at time 0 with 5D8/1 (FIG. 6A) and anti-CMV (FIG. 6B) mAbs; FIGS. 6C and 6D: staining of antrum biopsy from same patient at time 4 years with 5D8/1 (FIG. 6C) and anti-CMV (FIG. 6D) mAbs. 100× magnification.

DETAILED DESCRIPTION OF THE PRESENT INVENTION

The present inventor has surprisingly discovered that enteroviral capsid protein (VP1), RNA and cultivable viruses were present in the stomach biopsies of chronic fatigue syndrome (CFS) patients, most of whom have active symptoms termed functional dyspepsia or irritable bowel syndrome. Most of the patients developed an initial flu-like illness associated with, or soon followed by, gastrointestinal symptoms. Because enteroviruses are generally resistant to stomach acid, even swallowed, infectious respiratory secretions could infect the stomach or the lower intestinal tract. The demonstration of viruses in the tissues years after the initial infection lend strong evidence that these viruses are capable of chronic persistence, and can be causally related to the symptoms of CFS. The high sensitivity, specificity and positive predictive value of the VP1 staining procedure provides a simple, convenient diagnostic test for the presence of viral antigen in stomach tissue.

When testing is done in accordance with the teachings of the present invention positive results (defined as the detection of enteroviral antigen or nucleic acid) are then correlated with clinical systems. The combination of clinical symptoms consistent with CFS and the detection of enteroviral antigens in the patient's stomach (generally parietal cells) is diagnostic for CFS.

As the name chronic fatigue syndrome suggests, this illness is accompanied by fatigue. However, it's not the kind of fatigue patients experience after a particularly busy day or week, after a sleepless night or after a stressful event. It's a severe, incapacitating fatigue that isn't improved by bed rest and that may be exacerbated by physical or mental activity. It's an all-encompassing fatigue that results in a dramatic decline in both activity level and stamina.

People with CFS function at a significantly lower level of activity than they were capable of prior to becoming ill. The illness results in a substantial reduction in occupational, personal, social or educational activities.

The Centers for Disease Control (CDC) has published symptom criteria consistent with a diagnosis of CFS and include patients who present with six months or more of unexplained fatigue accompanied by other characteristic symptoms. These symptoms include: 1) cognitive dysfunction, including impaired memory or concentration, 2) post exertional malaise lasting more than 24 hours (exhaustion and increased symptoms) following physical or mental exercise, 3) unrefreshing sleep, 4) joint pain (without redness or swelling), 5) persistent muscle pain; 6) headaches of a new type or severity; 7) tender cervical or axillary lymph nodes and 8) sore throat.

In addition to the eight primary defining symptoms of CFS, a number of other symptoms have been reported by some CFS patients. The frequency of occurrence of these symptoms varies among patients. These symptoms include: irritable bowel, abdominal pain, nausea, diarrhea or bloating, chills and night sweats, brain fog, chest pain, shortness of breath, chronic cough, visual disturbances (blurring, sensitivity to light, eye pain or dry eyes), allergies or sensitivities to foods, alcohol, odors, chemicals, medications or noise, difficulty maintaining upright position (orthostatic instability, irregular heartbeat, dizziness, balance problems or fainting), psychological problems (depression, irritability, mood swings, anxiety, panic attacks), jaw pain, and weight loss or gain. Clinicians will need to consider whether such symptoms relate to a co-morbid or an exclusionary condition; they should not be considered as part of CFS other than they can contribute to impaired functioning.

The severity of CFS varies from patient to patient, with some people able to maintain fairly active lives. By definition, however, CFS significantly limits work, school and family activities.

While symptoms vary from person to person in number, type and severity, all CFS patients are functionally impaired to some degree. CDC studies show that CFS can be as disabling as multiple sclerosis, lupus, rheumatoid arthritis, heart disease, end-stage renal disease, chronic obstructive pulmonary disease (COPD) and similar chronic conditions.

CFS often follows a cyclical course, alternating between periods of illness and relative well-being. Some patients experience partial or complete remission of symptoms during the course of the illness, but symptoms often reoccur. This pattern of remission and relapse makes CFS especially hard for patients and their health care professionals to manage. Patients who are in remission may be tempted to overdo activities when they're feeling better, which can exacerbate symptoms and fatigue and cause a relapse. In fact, post exertional malaise is a hallmark of the illness.

The percentage of CFS patients who recover is unknown, but there is some evidence to indicate that the sooner symptom management begins, the better the chance of a positive therapeutic outcome. This means early detection and treatment are of utmost importance. CDC research indicates that delays in diagnosis and treatment may complicate and prolong the clinical course of the illness.

The present state-of-the-art for diagnosis CFS relies on a diverse and confusing combination of symptoms and is consequently not definitive. As a result physicians are often unable or unwilling to prescribe a therapeutic regime that will benefit their patients. Therefore there is a need for additional methods for making a more definitive diagnosis to give physicians the confidence necessary to initiate appropriate therapy and provide meaningful prognostic information to patients.

The present inventor has surprisingly discovered that the detection of enterovirus antigens or nucleic acids (enteroviral detection) in the stomach tissues of patients presenting with symptoms consistent with CFS and correlating these symptoms with enteroviral detection provides a more definitive CFS diagnosis. Consequently, physicians armed with this new method for diagnosing CFS can more confidently diagnosis, treat and provide prognoses for patients suffering with CFS.

EXAMPLES

Example 1

Immunoperoxidase Staining of Stomach Tissue for Detection Enteroviral Antigens

A total of 165 patients, fulfilling the Centers for Disease Control (CDC) criteria for Chronic Fatigue Syndrome (CFS) underwent upper GI endoscopies and antrum biopsies. Biopsies from stomach of normal volunteers (n=22, blinded samples, 13 female, 9 male) and other gastric diseases (n=12, 9 female, 3 male) served as controls: *Heliobacter pylori* gastritis (n=3); non-steroidal anti-inflammatory drug-induced gastritis (n=2); inflammatory bowel disease (n=1), eosinophilic gastritis (n=1), gastro-esophageal reflux disease (n=1), MALT lymphoma (n=2) and gastric carcinoma (n=2).

The biopsied tissue samples were placed in formalin, RNAlater® (Ambion, Inc. Austin, Tex.) or in normal saline and transported on ice and/or immediately frozen at −70° C. The formalin-fixed tissues can also be paraffin-embedded tissues cut into 4 micron pieces and mounted on microscope glass slides. The slides were dried at 60° C. for 30 minutes, deparaffinized with xylene and hydrated by passing through decreasing concentration of ethanol (100%, 95%, 80%) and PBS. Next, the tissues were treated with 3% hydrogen peroxide for 10 minutes, at room temperature (RT) to remove endogenous peroxidase activity.

Following treatment with hydrogen peroxide, the samples were placed in 10 mM sodium citrate buffer, pH 6.0, and heated under pressure (15 PSI) for 20 minutes to induce viral antigen epitope retrieval. Next the tissues were blocked with goat serum/BSA (3%) at RT, to decrease non-specific binding and then biotin, followed by avidin at RT, to reduce non-specific binding to endogenous biotin in stomach tissues.

The tissues were then incubated with appropriately diluted/titrated (1:2000 to 1:3000 of stock antibody) concentration of enterovirus group-specific anti-VP1 monoclonal antibody, such as, but not limited to 5D8/1 monoclonal antibody (available commercially from Dako, Carpenteria, Calif. catalogue number M7064) for 1 hour at 37° C. in a humidified chamber. Additional samples were stained with an anti-cytomegalovirus (CMV) mAb (Chemicon, Temecula, Calif.). The antibody-treated sample was then thoroughly washed in PBS-Tween, the slides are incubated with biotinylated goat anti-mouse antibody (ABC Kit from Zymed® available through Invitrogen, Carlsbad, Calif.) at RT for 30 minutes.

The slides were then washed again in PBS-Tween and incubated with avidin-horseradish peroxidase ABC reagent (Vector Laboratories) at RT for 30 minutes. After thorough washing in PBS-Tween, the slides were treated with DAB-chromogen (Vector Laboratories) at RT in a dark room, for 15 minutes. Next the slides were washed in tap water and counterstained with hematoxylin then washed again in PBS-Tween, passed through increasing concentration of ethanol, then fully dehydrated in xylene.

Figure 1:
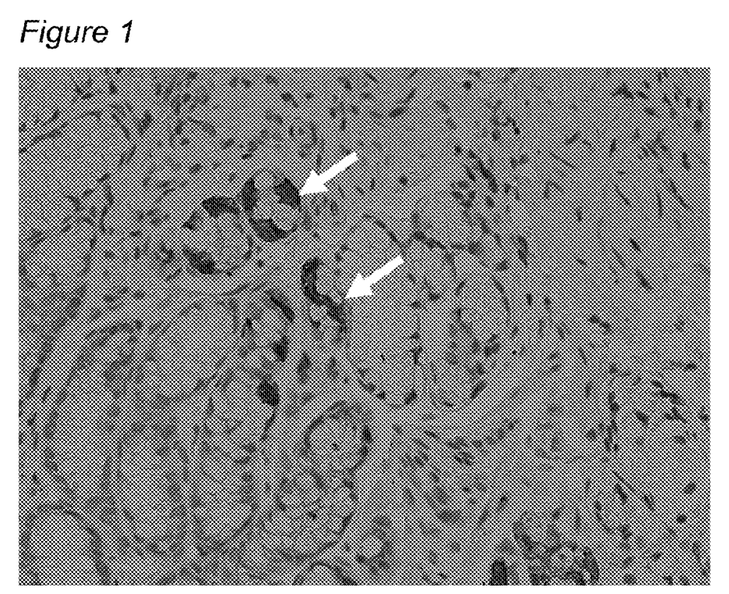
FIG. 1 depicts a positive immunoperoxidase enterovirus stain of parietal cells at 400× magnification (indicated by arrow) according to the teachings of the present invention.
Figure 2:
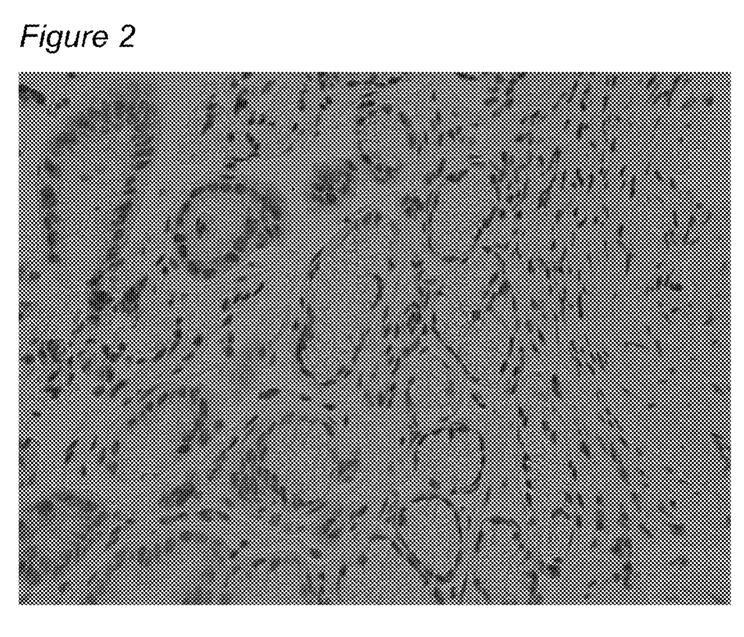
FIG. 2 depicts a negative immunoperoxidase enterovirus stain of parietal cells at 400× magnification according to the teachings of the present invention.

The slides were then dried, mounted with a coverslip and examined microscopically at 100×-400× magnification. FIG. 1 is a photomicrograph of a positive test result. The stained sections indicated by an arrow (peroxidase stained parietal cells) are foci of enteroviral viral antigens that have reacted specifically with the anti-enteroviral monoclonal antibody. Background staining represents uninfected tissues stained with hematoxylin. FIG. 2 depicts a negative result.

Figure 3:
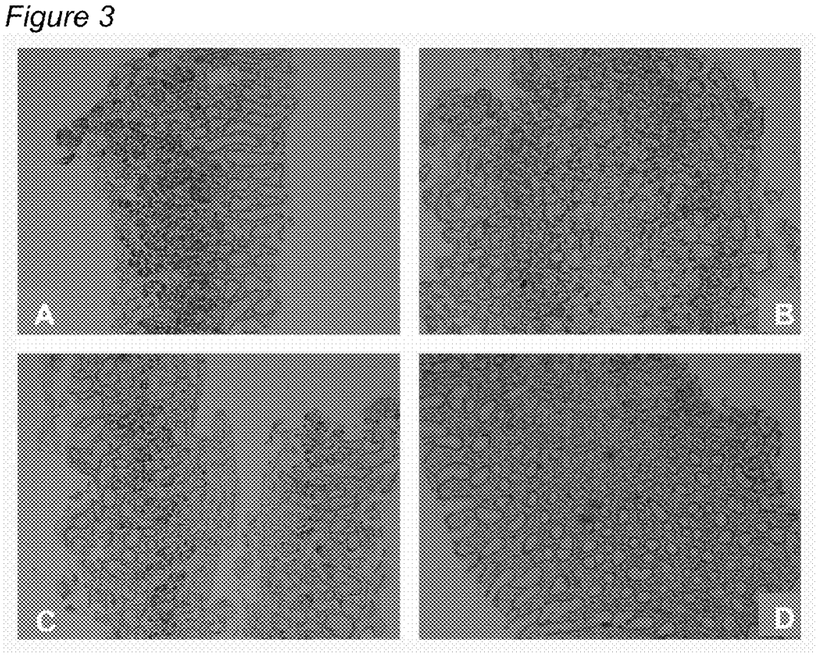
FIG. 3 depicts grading of immunoperoxidase staining with enterovisu-specific monoclonal antibodies (mAb) according to the teachings of the present invention. Immunoperoxidase staining was performed on antrum biopsy specimens. The degree of staining was classified as: 2+ if ≧50% of cells stained (FIGS. 3A and 3B); 1+ if >10% and <50% cells stained (FIG. 3C); 0 if none or rare cells stained with 5D8/1 mAb (FIG. 3D). 100× magnification.

The degree of staining was classified as: 0, none or rare staining with 5D8/1; 1+, >10% and <50% cells stained; 2+, 50% cells stained. FIG. 3 depicts grading of stained tissues.

Figure 4:
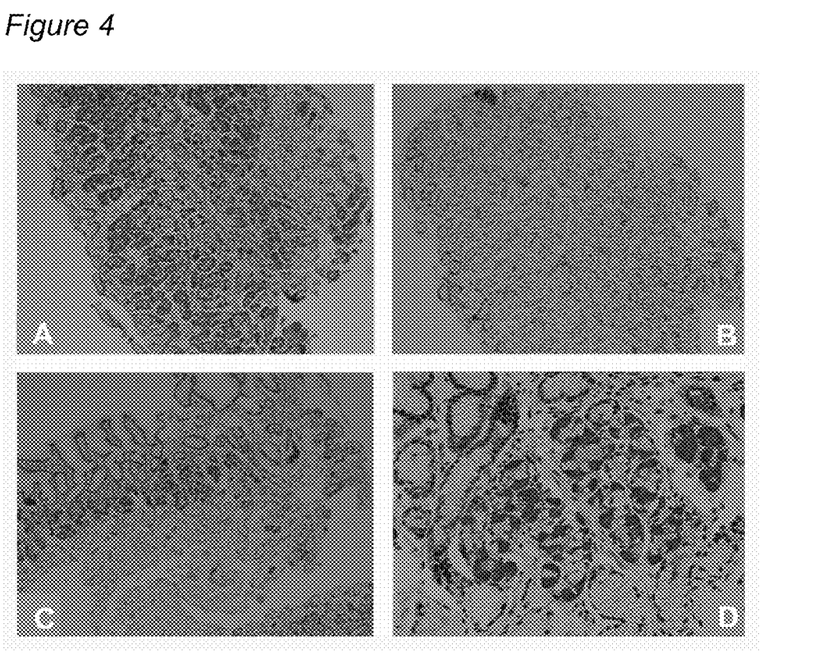
FIG. 4 depicts staining of antrum biopsies by virus-specific mAb 5D8/1 according to the teachings of the present invention.
Figure 5:
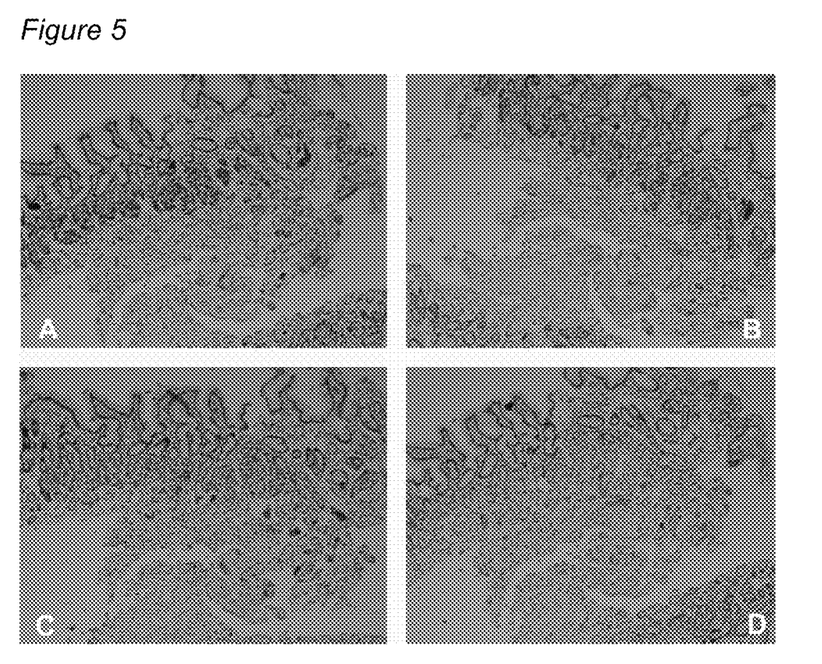
FIG. 5 depicts inhibition of 5D8/1 mAb binding in stomach tissue by an epitope-specific synthetic peptide according to the teachings of the present invention.
Figure 6:
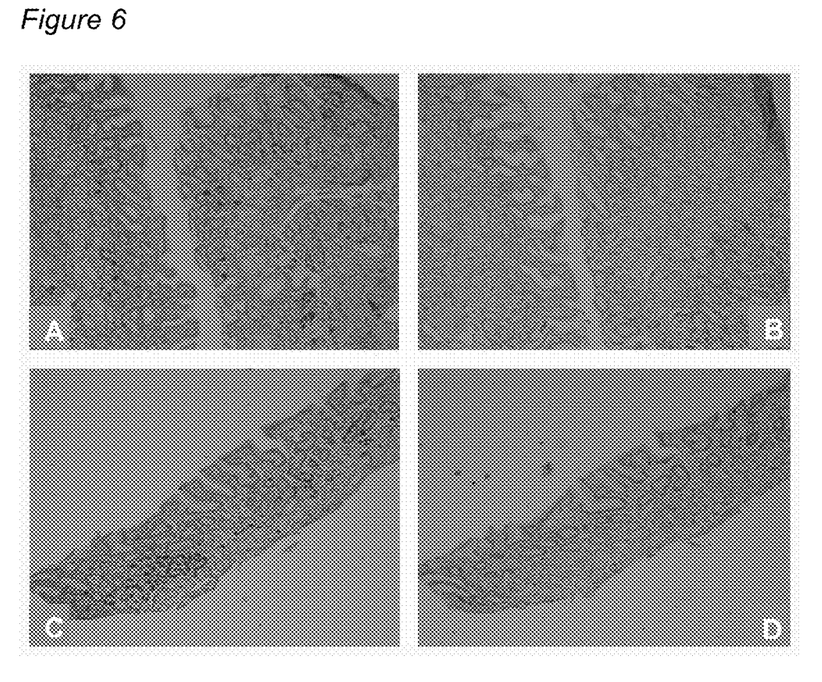
FIG. 6 depicts persistence of enterovirus in stomach biopsies in an individual taken four years apart according to the teachings of the present invention.

At the time of esophagogastroduodenoscopy, the majority of patients had mild, focal inflammation of the antrum, a few had normal-appearing mucosa and rare patients had diffuse erythema. A total of 157/165 (95%) biopsy specimens had microscopic evidence of mild chronic inflammation, whereas only 8/165 (5%) specimens showed the presence of *H. pylori* by specific staining. A total of 135/165 (82%) biopsy specimens stained positive for VP1 within parietal cells, whereas 7/34 (20%) of the controls stained positive (p≦0.001, $X^2$ test). A total of 88 (53%), 47 (29%) and 30 (18%) samples showed 2+, 1+ or 0 staining, respectively (FIG. 4). The sensitivity, specificity, positive and negative predictive values were 82%, 79%, 95% and 47%, respectively. Five of the eight biopsies which stained positive for *H. pylori* were also positive for VP1. Anti-CMV mAb failed to stain any of the biopsy specimens. Additionally, specific mAbs for varicella-zoster virus, parainfluenza viruses, adenovirus and respiratory syncitial virus failed to show staining in 10 VP1-positive specimens.

The degree of staining for VP1 within stomach biopsy tissues correlate with the severity of CFS symptoms. Furthermore, the degree of staining is inversely correlated with the ability of the patient to work.

Example 2

Peptide Inhibition Study

The binding epitope of the 5D8/1 antibody has been previously identified and a synthetic peptide representing this epitope was synthesized (Pro-Ala-Leu-Thr-Ala-Val-Glu-Thr-Gly-Ala-Thr-Asn-Pro-Leu-Val; SEQ ID NO: 1). Varying concentrations of the peptide inhibitor were preincubated with a titrated dose of 5D8/1 mAb at 37° C. for 30 min prior to performing the immunoperoxidase staining. Bovine serum albumin at 10 mg was used as a negative control.

The peptide inhibited the binding in a dose-dependent manner: 1 ng did not show significant inhibition, 10 ng partially inhibited the binding/staining and 100 ng completely blocked the antibody (FIG. 3). Bovine serum albumin did not inhibit binding of the antibody.

Example 3

Detection of Enteroviral RNA Using RT-RCR

Paraffin sections of antrum biopsy specimens from CFS patients and controls were processed with PureLink FFPE RNA isolation kit (Invitrogen); antrum biopsy specimens collected as described above and preserved in RNA-later® were homogenized in 1.5 ml of TriZol LS (Invitrogen). RNA was extracted from 250 µL of the suspension according to manufacturer's instructions.

Extracted RNA was amplified with biotinylated primers provided by pan-enterovirus oligodetect™ kit (Chemicon) using Qiagen one-step RT-PCR enzyme kit according to the standard instructions. The cDNA was detected by hybridizing with probe-coated plates and developed using streptavidin-conjugated with peroxidase followed by TMB-E. The optical density was determined at 450 nm in an EIA reader. In selected samples, the RNA was re-amplified using non-biotinylated primers (sense 5' CCT CCG GCC GAA TGC GGC TAA T 3' SEQ ID NO:2; antisense 5'CAA TTG TCA CCA TAA GCA GCC A 3' SEQ ID NO: 3). The gel-derived, purified 151 base pair cDNA produces were cloned into pDrive cloning vector and transformed into E. coli (PCR cloning kit, Qiagen). Plasmid inserts were sequenced by Retrogen (San Diego, Calif.).

Enterovirus (EV) RNA was detected in 9/24 (37%) paraffin-embedded samples form CFS patients; 1/21 controls had detectable EV RNA ($p<0.01$, Fisher exact test). One of three patients had detectable EV RNA from two samples taken four years apart (FIG. 4). Only 22/90 (24%) of the samples preserved in RNA-later were positive for EV RNA despite the much larger size of biopsy specimens (20-50 mg wet weight). When examined simultaneously, 19/63 of the samples stained 2+ had detectable EV RNA whereas 7/37 with 0 or 1+ staining were positive ($p=0.07$, Fisher exact test).

Example 4

Enterovirus Cultures of Stomach Tissue

BGMK cells were grown to 50-80% confluence in DMEM-2% fetal bovine serum (FBS) before incubation in the presence of 50 µg/ml of 5-idoxyuridine (5-idu) for 48 hours. After removal of the 5-IDU-containing medium, the cells were fed with DMEM-2% FBS, containing $10^{-6}$ M of dexamethasone (dex-DMEM).

Stomach biopsy specimens, frozen in normal saline, were ground in Opti-Pro. The homogenate was frozen in ethanol/dry ice bath and thawed in 37° C. water bath three times. A 250 µL portion of the cell lysate was inoculated onto cell monolayer previously treated with dex-DMEM for at least 24-48 hours. After 1 hour of incubation 25° C., the cell lysates were removed and replaced with dex-DMEM. The inoculated cells were re-fed weekly with dex-DMEM. After 4-6 weeks of incubation, the cell monolayers were scraped or trypsinized for enteroviral RNA detection using the procedure described above. The cleared lysates of scraped cells from 6-week old cultures were passed into a new set of 5-idu, dex-treated BGMK cell cultures to demonstrate the infectivity of the virus product The cells were also examined for the presence of viral protein by IFA using 5 D8/1 as the primary antibody and standard staining technique.

VP1 staining, RNA analysis and cultures were simultaneously performed on 75 specimens. Table 1 depicts the results of VP1 staining and EV RNA detection from the first 13 patients. When incubated with normal BGMK cells for 4 weeks, none of the tissue lysates yielded detectable viral RNA. In 4-week BGMK cultures previously treated with 5-idu and dexamethasone, few biopsy specimens yielded detectable EV RNA. EV RNA was detected with higher frequency and intensity at 6 weeks but gradually disappeared as cultures were carried out to 8-12 weeks.

No significant cytopathic effect was seen in the EV RNA-positive cultures, whereas wild type strains of enteroviruses would cause major cytopathic changes within one week. When the cleared cell lysates of the 6-week infected primary cultures were passed to another set of uninfected 5-idu-, dex-treated BGMK cells. EV RNA was detected in several of the cultures at 4 weeks but disappeared at 8 weeks. The 151 base pair cDNA isolated from five of the positive cultures were confirmed to be EV RNA by sequencing.

TABLE 1

| | | | | BGMK cell culture | | | | | |
| | | | | Normal cells | 5-idu, dex-treated cells | | | | |
| | | | | | Primary culture* | | | 1st pass† | |
| Patient No. | # yrs sick | VP1 stain | EV RNA | 4 wk | 4 wk | 6 wk | 8 wk | 4 wk | 8 wk |
|---|---|---|---|---|---|---|---|---|---|
| 1 | 5- | − | − | − | ++ | +++ | − | +++ | − |
| 2 | 4 | nd | nd | − | − | +++ | − | ++ | − |
| 3 | 6 | ++ | + | − | − | +++ | +++ | + | − |
| 4 | 10 | ++ | + | − | ++ | ++ | − | +++ | − |
| 5 | 12 | ++ | + | − | − | ++ | − | ++ | − |
| 6 | 4 | + | − | − | − | + | − | nd | − |

TABLE 1-continued

| | | | | BGMK cell culture | | | | | |
| --- | --- | --- | --- | --- | --- | --- | --- | --- | --- |
| | | | | Normal cells | 5-idu, dex-treated cells | | | | |
| | | | | | Primary culture* | | | 1$^{st}$ pass† | |
| Patient No. | # yrs sick | VP1 stain | EV RNA | 4 wk | 4 wk | 6 wk | 8 wk | 4 wk | 8 wk |
| 7 | 8 | − | nd | − | +++ | ++ | ++ | + | − |
| 8 | 6 | nd | − | − | − | + | − | − | − |
| 9 | 10 | + | +++ | − | + | ++ | ++ | ++ | − |
| 10 | 13 | + | − | − | + | nd | nd | nd | nd |
| 11 | 3 | ++ | − | − | − | nd | nd | nd | nd |
| 12 | 15 | ++ | ++ | − | − | nd | nd | nd | nd |
| 13 | 20 | − | − | − | − | nd | nd | nd | nd |

5-idu, 5-idoxyuridine; dex, dexamethasone; EV, enterovirus; VP1, viral capsid protein 1
Three to four biopsies were obtained from each patient's antrum and processed for CP1, RNA assay and viral culture. EV RNA was determine on the RNA-later specimens and culture lysates at periods indicated. The optical density ready of the RT-RNA ELISA was rated as: + if >1.0 and <1.9; ++ if >2.0 and <3.0; +++ if ≧3.0; nd = not done.
*The tissue homogenates were inoculated onto untreated BGML cells (normal) or 5-idu-and dex-treated BGMK cells; half of the tissue culture monolayers were scraped and lysed and EV RNA determined at the time period indicated.
†Lysates from the 6-week primary cultures were passed to another set of uninfected, 5-idu- and dex-treated cells, and the presence of EV RNA was assayed at the time period indicated.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

REFERENCES CITED

1. Fukuda K, Straus S E, Hickie I, et al and the International Chronic Fatigue Syndrome Study Group. The chronic fatigue syndrome: a comprehensive approach to its definition and study. Ann Intern Med. 1994; 121:953-59
2. Reeves W C et al. Identification of ambiguities in the 1994 chronic fatigue syndrome research case definition and recommendations for resolution. BMC Health Serv Res. 2003; 3:25-9.
3. Komaroff A L, Gupta S, Salit I E. Post-viral fatigue syndrome in: Ablashi D V, Faggioni A, Keiger G R F, Pagano J S, Pearson G R, eds. Epstein-Barr virus and human disease 1988. Clifton, N.J.: The Human Press, 1989:235-53
4. Levy J A. Viral studies of chronic fatigue syndrome: Introduction. Clin Infect Dis. 1994; 18(suppl 1):S117-2
5. Chia J K S, Chia L Y. Chronic *Chlamydia pneumoniae* infection, a treatable cause of chronic fatigue syndrome. Clin Infect Dis. 1999; 29:452-3
6. Lerner M A, Zervos M, Dworkin H J, Chang C H, Fitzgerald J T, Goldstein J, Lawrie-Hoppen C. et al. New cardiomyopathy: pilot study of intravenous ganciclovir in a subset of chronic fatigue syndrome. Infect Dis. Clin Prac. 1997; 6:110-117

7. Kerr J R, Cunniffe V S, Kelleher P, Berstein R M, Bruce I N. Successful intravenous immunoglobulin therapy in 3 cases of Parvovirus B19-associated chronic fatigue syndrome. Clin Infect Dis. 2003; 36:e100-6
8. Chia J K S, Jackson B. Myocarditis due to parvovirus B19 in an adult patient. Clin Infect Dis. 1996; 23:200-1
9. Chia J K, Chia A. Diverse etiologies for the chronic fatigue syndrome. Clin Infect Dis. 2003; 36:671-2
10. Yousef G E, Mann G F, Smith D F, Bell E J, McCartney R A. Chronic enterovirus infection in patients with postviral fatigue syndrome. Lancet 1988; 1:146-7
11. Landay A L, Jessop C, Lennette E T, Levy J A. Chronic fatigue syndrome: clinical condition associated with immune activation. Lancet 1991; 338:707-12
12. Miller N A, Carmichael H A, Calder B D, et al. Antibody to Coxsackie B virus in diagnosing post-viral fatigue syndrome. BMJ; 302:140-3
13. Halpin D, Wessely S. VP1 antigen in chronic postviral fatigue syndrome (letter). Lancet 1989; 1:1028-1029
14. Manian F A. Simultaneous measurement of antibodies to Epstein-Barr virus, human herpesvirus 6, herpes simplex virus type 1 and 2, and 14 enteroviruses in chronic fatigue syndrome: is there evidence of activation of a nonspecific polyclonal immune response. Clin Infect Dis. 1994; 19:448-53
15. Swanink C M, Melchers W J, van der Meer J W, Vercoulen J H, Bleijenberg G, Fennis J F, Galama J M. Enterovirus and the chronic fatigue syndrome. Clin Infect Dis 1994; 19:860-4
16. Minor P D, Bell E J (1990): Picornaviridae. In: "Principle of bacteriology, virology and immunology, 8$^{th}$ edition." Collier L H, Timbury M C (eds). London: Arnold Publisher, pp 323-356
17. Nairn C, Galbraith D N, Clements G B. Comparison of Coxsackie B neutralization and enteroviral PCR in chronic fatigue patients. J Med Virol. 1995 46:310-313
18. Behan P O, Behan W M H, Bell Ej. The post-viral fatigue syndrome-an analysis of the findings in 50 cases. J Infect. 1985; 10:211-222
19. Gow J W, Behan W M H, Clements G B, Woodall C, Riding M, Behan P O. Enteroviral RNA sequences detected by polymerase chain reaction in muscle of patients with post-viral fatigue syndrome. BMJ 1991; 302:692-6
20. Gow J W, Behan W M H, Simpson K, McGarry F, Keir S, and Behan P O. Studies on enterovirus in patients with chronic fatigue syndrome. Clin Infect Dis 1994; 18 (Suppl):S126-129
21. Yousef G E, Isenberg D A, Mowbray J F. Detection of enteroviral-specific RNA sequence in muscle biopsy specimens from patients with adult-onset myositis. Ann Rheum Dis 1990; 49:310-5
22. Cunningham L, Bowles N E, Lane R J M, Dubowitz V, Achard L C. Persistence of enteroviral RNA in chronic fatigue syndrome is associated with abnormal production of equal amounts of positive and negative strands of enteroviral RNA. J Gen Virol. 1990; 71, 1399-1402
23. Galbraith D N, Nairn C, Clements G B. Phylogenetic analysis of short enteroviral sequences from patients with chronic fatigue syndrome. J Gen Virol. 1995; 76:1701-1707
24. McArdle A, McArdle F, Jackson M J, Page S F, Fahal I, Edwards R H. Investigation by polymerase chain reaction of enteroviral infection in patients with chronic fatigue syndrome. Clin Sci. 1996; 90:295-300
25. Lindh G, Samuelson A, Hedlund K O, Evengard B, Lindquist L, Ehrnst A. No finding of enteroviruses in Swedish patients with chronic fatigue syndrome. Scan J Infect Dis 1996; 28:305-7
26. Lane R J, Soteriou B A, Zhang H, Archard L C. Enterovirus related metabolic myopathy: a postviral fatigue syndrome. J Neurol Neurosurg Psychiatry 2003; 74:1382-6
27. Douche-Aourik F. et al. Detection of enterovirus to human skeletal muscle from patients with chronic inflammatory muscle disease or fibromyalgia and healthy subjects. J Med Virol. 2003; 71:540-7
28. Chia J K, Jou N S, Majera L, et al. The presence of enteroviral RNA (EV RNA) in peripheral blood mononuclear cells (PBMC) of patients with the chronic fatigue syndrome (CFS) associated with high levels of neutralizing antibodies to enteroviruses. Abstract 405, Clin Infect Dis. 2001; 33:1157
29. Chia J, Chia A. Detection of enteroviral RNA in the peripheral blood leukocytes of patients with the chronic fatigue syndrome. Abstract 763. In: Program and abstracts of the 40$^{th}$ annual meeting of the Infectious Diseases Society of America. Chicago, Ill. IDSA 2002: 178
30. Chia J, Chia A. Detection of double-stranded RNA in the peripheral blood leukocytes of patients with the chronic fatigue syndrome. Abstract T-101. In Program of the 104$^{th}$ General Meeting for the American Society of Microbiology. New Orleans, La., 2004
31. Chia J, Chia A. Ribavirin and Interferon α for the treatment of patients with chronic fatigue syndrome associated with chronic Coxsackievirus B infection: a preliminary observation. J. Appl. Research. 2004; 4:286-292
32. Chia, J K. The role of enterovirus in chronic fatigue syndrome. J. Clin. Path. 2005; 58:1126-1132

I claim:

1. A method for diagnosing chronic fatigue syndrome (CFS) in a human patient comprising:

detecting enteroviruses in the stomach tissue of a patient having symptoms consistent with CFS wherein said symptoms consist of persistent fatigue for at least six months and at least four further symptoms selected from the group consisting of cognitive dysfunction, post-exertional malaise, unrefreshing sleep, joint pain, persistent muscle pain, headaches, tender cervical or axillary lymph nodes and sore throat; and correlating the detection of said enterovirus with said symptoms to establish a diagnosis of CFS in said human patient.

2. The method according to claim 1 wherein said detecting step comprises detection of enteroviral capsid protein (VP 1) or enteroviral viral RNA in said stomach tissue of said patient.

3. The method according to claim 1 wherein said enterovirus detected in said detecting step is a non-cytopathic enterovirus.

4. The method according to claim 2 wherein said detecting method comprises immunoperoxidase or immunofluorescent staining of said stomach tissue.

5. The method according to claim 2 wherein said detecting method comprises detecting viral RNA within said stomach tissue using RT-PCR.

6. The method according to claim 2 wherein said detecting method comprises co-culturing stomach tissue with buffalo green monkey kidney cells.

* * * * *